(12) United States Patent
Thomas

(10) Patent No.: US 10,702,031 B2
(45) Date of Patent: Jul. 7, 2020

(54) PANEL BRACELET WITH REPLACEABLE INSERTED PANELS

(71) Applicant: Michael Thomas, Centerbrook, CT (US)

(72) Inventor: Michael Thomas, Centerbrook, CT (US)

(*) Notice: Subject to any disclaimer, the term of this patent is extended or adjusted under 35 U.S.C. 154(b) by 244 days.

(21) Appl. No.: 15/394,769

(22) Filed: Dec. 29, 2016

(65) Prior Publication Data

US 2017/0231338 A1 Aug. 17, 2017

Related U.S. Application Data

(63) Continuation-in-part of application No. 14/742,379, filed on Jun. 17, 2015, now abandoned.

(60) Provisional application No. 62/013,256, filed on Jun. 17, 2014.

(51) Int. Cl.
| | |
|---|---|
| *A44C 5/00* | (2006.01) |
| *A44C 17/02* | (2006.01) |
| *A44C 15/00* | (2006.01) |
| *A61B 5/00* | (2006.01) |
| *F23Q 2/00* | (2006.01) |
| *G04G 17/08* | (2006.01) |
| *G04G 21/02* | (2010.01) |

(52) U.S. Cl.
CPC ........ *A44C 17/0216* (2013.01); *A44C 5/0007* (2013.01); *A44C 5/0015* (2013.01); *A44C 5/0053* (2013.01); *A44C 5/0084* (2013.01); *A44C 15/0025* (2013.01); *A61B 5/681* (2013.01); *F23Q 2/00* (2013.01); *G04G 17/08* (2013.01); *G04G 21/025* (2013.01)

(58) Field of Classification Search
CPC ................................ A44C 5/00; A44C 5/0007
See application file for complete search history.

(56) References Cited

U.S. PATENT DOCUMENTS

| | | | |
|---|---|---|---|
| 4,087,989 | A | 5/1978 | Taran |
| 4,862,435 | A | 8/1989 | Reichel et al. |
| 6,571,578 | B2 | 6/2003 | Akyol |
| 6,629,434 | B2 | 10/2003 | Chia et al. |
| 7,036,339 | B1 | 5/2006 | Chia et al. |
| 7,409,837 | B2 | 8/2008 | Smith |
| 8,371,141 | B2 | 2/2013 | Richmond |
| 2005/0189906 | A1 | 9/2005 | Sun |
| 2007/0194066 | A1* | 8/2007 | Ishihara ............... A44C 5/0015 224/164 |
| 2010/0300146 | A1 | 12/2010 | Klecka |
| 2011/0185611 | A1 | 8/2011 | Adams |
| 2012/0087216 | A1 | 4/2012 | Keung |
| 2012/0138637 | A1 | 6/2012 | Ciavarella |

(Continued)

OTHER PUBLICATIONS

Italiancharms, www.italiancharms.com.

*Primary Examiner* — Emily M Morgan
(74) *Attorney, Agent, or Firm* — Blynn L. Shideler; BLK Law Group

(57) ABSTRACT

A panel bracelet includes a plurality of panels configured to be selectively replaceable within the bracelet, and a pair of panel holding frames, wherein each open panel holding frame is configured to hold a panel therein. Each panel holding frame includes a retaining bead that is received within a perimeter groove of the panel which is held within the panel holding frame to receive and retain the panel therein.

10 Claims, 9 Drawing Sheets

(56) References Cited

U.S. PATENT DOCUMENTS

| | | |
|---|---|---|
| 2012/0234043 A1 | 9/2012 | Guerrero, II |
| 2014/0090418 A1 | 4/2014 | Mihalyo |
| 2014/0298858 A1 | 10/2014 | Chang |
| 2015/0277489 A1* | 10/2015 | Lin .................. G06F 1/163 361/679.03 |
| 2015/0359304 A1 | 12/2015 | Thomas |

* cited by examiner

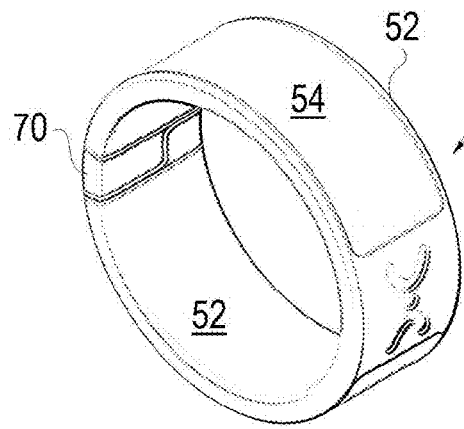
FIG. 18A
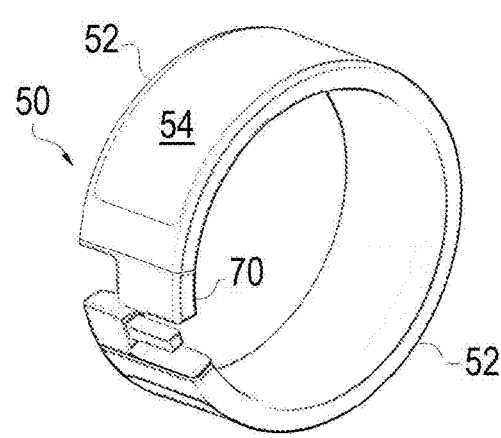
FIG. 18B
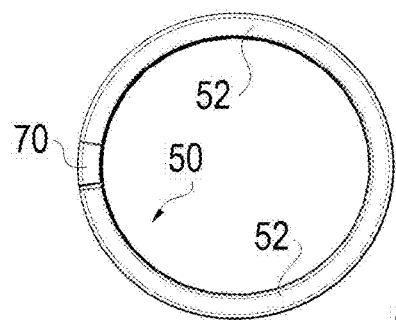
FIG. 18C
FIG. 18D
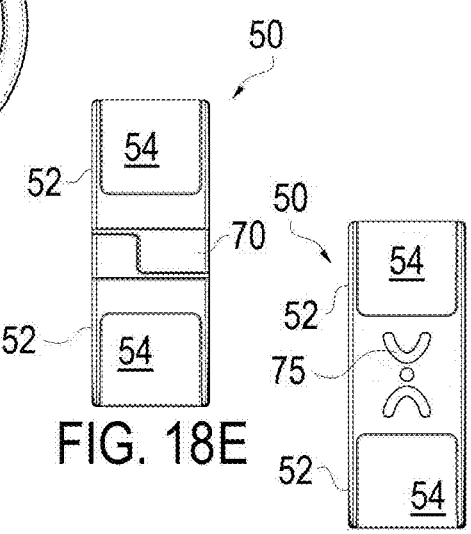
FIG. 18E
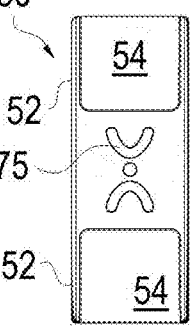
FIG. 18F
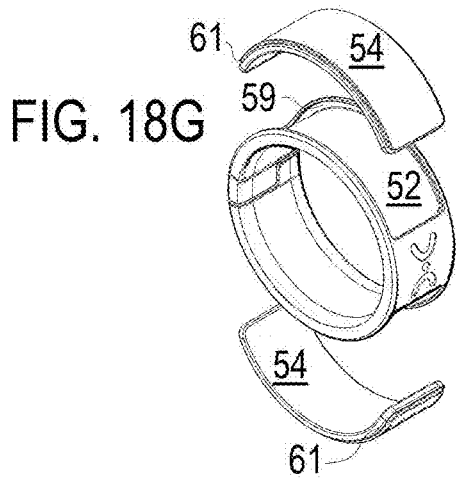
FIG. 18G
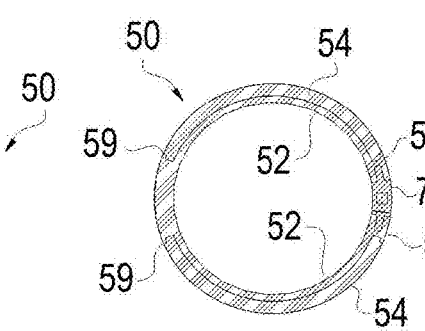
FIG. 18H
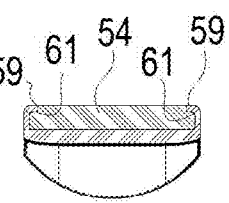
FIG. 18I

PANEL BRACELET WITH REPLACEABLE INSERTED PANELS

RELATED APPLICATIONS

The present application is a continuation in part of U.S. patent application Ser. No. 14/742,379 which published Dec. 17, 2015 as U.S. Publication 2015-0359304, which is incorporated herein by reference. U.S. patent application Ser. No. 14/742,379 claims the benefit of Provisional Patent application Ser. No. 62/013,256 filed on Jun. 17, 2014 and entitled "Reversible Panel Bracelet with Two Sided Inserted Panels" which is incorporated herein by reference.

BACKGROUND OF THE INVENTION

1. Field of the Invention

The present invention relates to jewelry, specifically to a panel bracelet with replaceable inserted panels.

2. Background Information

The word "jewelry" is derived from the Latin word jocale, meaning "plaything," and the word jewel, which was anglicized during the 13th century from the Old French word "jouel." The word "jewelry" (spelled jewellery in European English) is used to describe any piece of precious material (gemstones, noble metals, etc.) used to adorn one's self. Jewelry has played a constant and significant part of human history.

Through-out human history, irrespective of religion, race, or culture, jewelry has existed as an integral form of expression, wealth and social status. While the materials and techniques used to manufacture jewelry have in many ways evolved, there are also a number of similarities with the very first forms of jewelry worn, according to some estimates, an astounding 75,000 to 100,000 years ago. Relatively recently discovered mollusk or nassarius kraussianus shells that had been perforated to be strung together are now thought to be some of the oldest known man-made jewelry dating back to the Middle Stone Age, some 75,000 to 100,000 years ago. In the late 1800s, British archaeologist Archibald Campbell Carlyle said of primitive man that "the first spiritual want of a barbarous man is decoration." More than just a curio from the past, jewelry, like art, is a window into the soul of humanity, and a poignant reminder of that which separates humankind from the animal kingdom—a desire to capture the essence of beauty, to possess its secrets, and to unlock its mysteries.

Bracelets are a type of jewelry worn around the wrist, and less commonly around the ankle (although this subset of jewelry is technically referenced as "anklets"), of the user and themselves have a long and storied history. Many scholars cite that the earliest known bracelets hark back to 2500 BC, worn by the ancient Sumerians of Southern Mesopotamia. Other sources suggest that "bracelets first worn in 4700 BC during the reign of King Zer were constructed from gold and manufactured in a style widely available today." Clearly, bracelets were worn long before the even term bracelet was established. Dr. Mark Clayson has described that "during ancient Grecian times, soldiers wore defensive bands of leather often decorated with gold, silver, and other gemstones on their forearms called Bracels, from the Latin term for arm, "Brachium". The Grecian women realized that these accessories would look good on them, so they began wearing smaller versions—called Bracel-ets."

One type of common bracelet may be called a panel bracelet and is one utilizing at least one and generally a series of decorative panels coupled along the bracelet. FIG. 1 illustrates what has been called an antique panel bracelet 10 and includes a series of rectangular frames 12 holding individual decorative porcelain or ivory panels 14. The frames 12 are also called bezels or mounts and may be pivotally coupled together through links or a hinge such as shown in FIG. 1.

A conventional clasp or connection may be provided on the respective ends of the bracelet 10 to allow the bracelet 10 to be coupled around the wrist of the user. Other bracelet designs are a continuous hoop which is slipped over the user's wrist, and these may also incorporate a clasp that acts to shorten the hoop to secure the bracelet in place (such as found in many wrist watch designs).

FIG. 2 illustrates a panel bracelet from the 1980s which attaches two distinct decorative Lucite panels 14 on opposed sides of each gold plated frame 12. This design allows the user to selectively reverse the bracelet 10 as desired, to give the user greater flexibility in the appearance of the bracelet 10 and thus greater utility in the bracelet 10.

FIG. 3 illustrates a known panel bracelet 10 design that is called an Italian modular charm bracelet, such as available at www.italiancharms.com. This panel bracelet 10 uses stainless steel rectangular link frames 12 to which are coupled decorative panels 14, called "Charms" formed of decorative enamel, cubic zirconia, and natural or faux stones. The frames 12 and associated charms or panels 14 are intended to be easily and quickly interchangeable by the wearer. Further, the variety of available "charms" or panels 14 allows the user to build their own bracelet 10 and the developers have incorporated an on-line simulation to allow the user to see how their custom bracelet 10 design will look to aid in its design.

FIG. 4 illustrates a known panel bracelet 10 design that is called a "boozy wisdom" bracelet. In this panel bracelet 10 the panels 14 are essentially integral with the frame 12 to provide a reversible bracelet 10 which is comprised of four panels 14, each inscribed on either side with a variety of cheeky phrases, such as "Good form, but not formality" alongside an image of a shapely woman, and a tiny beer stein decorates a panel that reads "To our wives and sweethearts, may they never meet." As with the panel bracelet 10 of FIG. 2, this design allows the user to selectively reverse the bracelet 10 as desired, to give the user greater flexibility in the appearance of the bracelet 10 and thus greater utility in the bracelet 10.

FIG. 5 illustrates an antique panel bracelet 10 from the 1930's and includes a series of rectangular filigree frames 12 holding individual decorative panels 14. The panels 14 in this bracelet 10 are bone and referenced as storyteller scrimshaw. Scrimshaw itself has its own fascinating history.

FIG. 6 illustrates an antique panel bracelet 10 called a memory frame bracelet with nickel plated frames 12 receiving images, such as sepia 19th Century female transfers, forming panels 14 within the meaning of this application.

The patent literature also discloses a number of bracelet developments, such as U.S. Pat. Nos. 7,036,339 and 6,629,434 which are incorporated herein by reference and disclose a decorative jewelry module that comprises a base member with a hollow interior, a decorative insert, and a fastener arrangement. The decorative insert is sized in relation to the interior of the base member so as to be placed within the hollow base member and viewed through the top opening and wherein number of such units may be connected in series to form a tennis bracelet.

U.S. Pat. No. 4,862,435, which is incorporated herein by reference, discloses a combination bracelet and wristwatch.

U.S. Pat. No. 7,409,837, which is incorporated herein by reference, discloses an interchangeable jewelry insert having an extension formed of elastic material that can frictionally engage a surface of a receptacle for receiving the insert.

U.S. Pat. No. 7,703,974, which is incorporated herein by reference, discloses a watch with a reversible body.

U.S. Pat. No. 8,366,313, which is incorporated herein by reference, discloses jewelry in the form of a watch band with replaceable watch body in an effective and efficient cage and core configuration.

U.S. Pat. No. 8,371,141, which is incorporated herein by reference, discloses jewelry which includes a decorative insert body and a receiving portion that includes an opening for receiving the decorative insert body. For example, the decorative insert body may include magnetic material and the receiving portion includes a rear portion including ferromagnetic material.

U.S. Pat. No. 6,571,578, which is incorporated herein by reference, discloses a reversible ornamental article of jewelry having a plurality of ornamental links hinge ably secured to one another to form a flexible strand of jewelry, which can be in the form of a necklace or bracelet.

U.S. Patent Application Publication Number 2010-0300146, which is incorporated herein by reference, discloses a decorative charm that is designed to reversibly attach to an elastic band wherein the design of the decorative item described herein that facilitates its reversible attachment to an elastic band or bracelet.

U.S. Patent Application Publication Number 2014-0090418, which is incorporated herein by reference, discloses an undulating perimeter rubber base bracelet with charms locked in sockets.

U.S. Patent Application Publication Number 2012-0138637, which is incorporated herein by reference, discloses a bracelet with integral spray mechanism.

U.S. Patent Application Publication Number 2007-0194066, which is incorporated herein by reference, discloses a bracelet with a snap in electronic element such as a watch or global positioning system.

U.S. Patent Application Publication Number 2002-0194867, now U.S. Pat. No. 6,571,578, which is incorporated herein by reference, discloses a bracelet with reversible elements hinged to each other along the bracelet body.

Bracelets form an ongoing important part of the story of humanity and there is an ongoing desire to give individuals new tools for expressing their desire for ornamentation. Improvements in panel bracelet design further these desires.

SUMMARY OF THE INVENTION

Some of the objects of the invention are achieved with a flexible reversible bracelet with inserted two sided panels according to the present invention.

One embodiment of the invention provides a reversible bracelet with inserted two sided panels formed of a series of open insert or panel holding frames, wherein each frame is designed to hold a two sided panel therein with each side of the panel including an ornamental design. Each open frame may be formed of a rubber or silicon or similar materials and generally "C" shaped in cross section to receive and retain one of the two sided panels therein, which may be snap or press fit into the frame. Each frame/panel may be pivoted relative to the adjacent frame/panel to provide selective reversibility to the bracelet or the bracelet may be flipped in its entirety. The panels may be formed of two separate facing halves coupled together and may be designed by the user's themselves in an on-line panel creation system. The panels may have sports motifs, may be formed as watches, key-holding units, electronic devices, sports trading cards, convertible to toys, etc.

One embodiment of the present invention provides a panel bracelet comprising an elastomeric body having two rectangular panel holding frames, wherein each frame is designed to hold a panel therein wherein each panel holding frame is i) generally "C" shaped in cross section to receive and retain one of the panels therein and which are press fit into the frame, or ii) includes a retaining bead that is received within a matching groove in the associated panel to receive and retain one of the panels therein and which are press fit into the frame, and a plurality of panels associated with the panel bracelet and removeably secured within the rectangular panel holding frames.

One embodiment of the present invention provides a panel bracelet comprising: a plurality of panels configured to be selectively replaceable within the bracelet, wherein each panel includes parallel ends configured to be perpendicular to the width of the bracelet and longer parallel sides configured to extend along the circumference of the bracelet, wherein each panel includes a perimeter groove around the perimeter of the panel; a pair of panel holding frames, wherein each open panel holding frame is configured to hold a panel therein, and wherein each panel holding frame includes a retaining bead that is received within the perimeter groove of a panel held within the panel holding frame to receive and retain the panel therein.

One embodiment of the present invention provides a reversible panel bracelet comprising: a plurality of two sided panels configured to be selectively replaceable within the bracelet and having each side of the panel selectively viewable from one side of the bracelet and with each side of the panel including an ornamental design; a series of open panel holding frames, wherein each open panel holding frame includes a central opening through the bracelet and is designed to hold a two sided panel therein, wherein with one open panel holding frame holding one two sided panel therein then one side of the two sided panel held within the open panel holding frame is viewable from one side of the bracelet and simultaneously the other side of the two sided panel held within the open panel holding frame is viewable from the other side of the bracelet via the central opening of the open panel holding frame; and wherein each panel holding frame is one of i) generally "C" shaped in cross section to receive and retain one of the two sided panels therein and which are placed within the open panel holding frame, or ii) includes a retaining bead that is received within a matching groove in perimeter of a panel held within the open panel holding frame to receive and retain one of the two sided panels therein.

One embodiment of the present invention provides a panel bracelet comprising an elastomeric body having exactly two substantially rectangular panel holding frames, wherein each frame is designed to hold a panel therein and wherein each panel holding frame is one of i) generally "C" shaped in cross section to receive and retain one of the panels therein, or ii) includes a retaining bead that is received within a matching groove in the perimeter of an associated panel to receive and retain one of the panels therein, and a plurality of panel associated with the panel bracelet and removeably secured within the rectangular panel holding frames, wherein the plurality of panels include at least two from the group i) a panel which includes electronic components, ii) a panel which includes a watch, iii) a panel which is in the form of a collectable sports related element, iv) a panel which includes a USB key, v) a panel which includes at least one biometric sensor, vi) a panel which includes a user identifying barcode, vii) a panel which includes a lighter, viii) a panel which includes a series of tools folded into the panel, and ix) a panel which includes a pump spray container.

These and other advantages of the present invention will be clarified in the brief description of the preferred embodiment taken together with the drawings in which like reference numerals represent like elements throughout.

BRIEF DESCRIPTION OF THE DRAWINGS

FIG. 18A is a perspective schematic view of a bracelet with inserted panels according to one aspect of the present invention;

FIG. 18B is a perspective schematic view of the bracelet of FIG. 18A with the clasp open;

FIG. 18C is a schematic elevational side view of the bracelet of FIG. 18A;

FIG. 18D is a schematic top plan view of the bracelet of FIG. 18A;

FIG. 18E is a schematic elevational clasp end view of the bracelet of FIG. 18A;

FIG. 18F is a schematic elevational opposite end view of the bracelet of FIG. 18A;

FIG. 18G is a perspective, partially exploded, schematic view of the bracelet of FIG. 18A;

FIG. 18H is a schematic elevational circumferential section view of the bracelet of FIG. 18A;

FIG. 18I is a schematic transverse section view of a frame and panel of the bracelet of FIG. 18A;

DESCRIPTION OF THE PREFERRED EMBODIMENTS

Figure 7A:
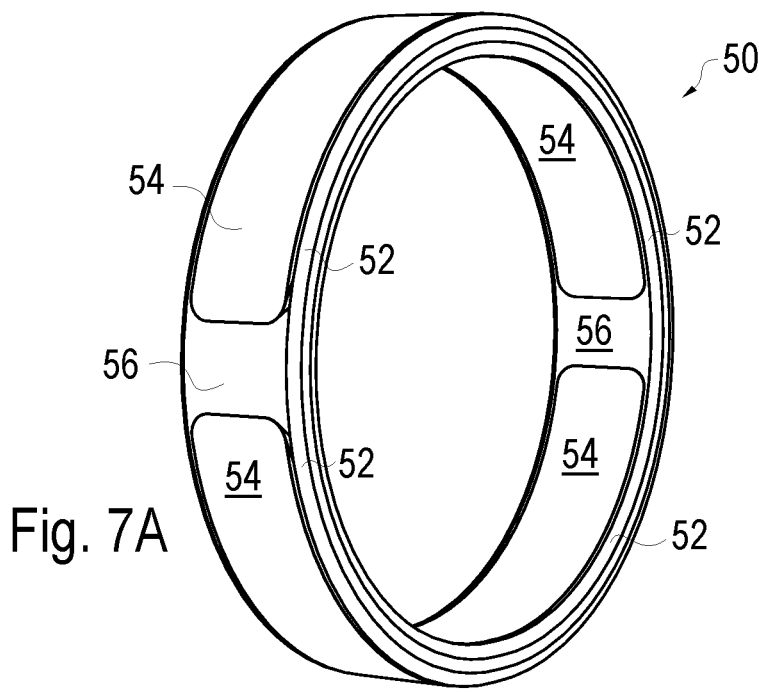
FIG. 7A is a perspective schematic view of a reversible bracelet with inserted panels according to one aspect of the present invention.
Figure 7B:
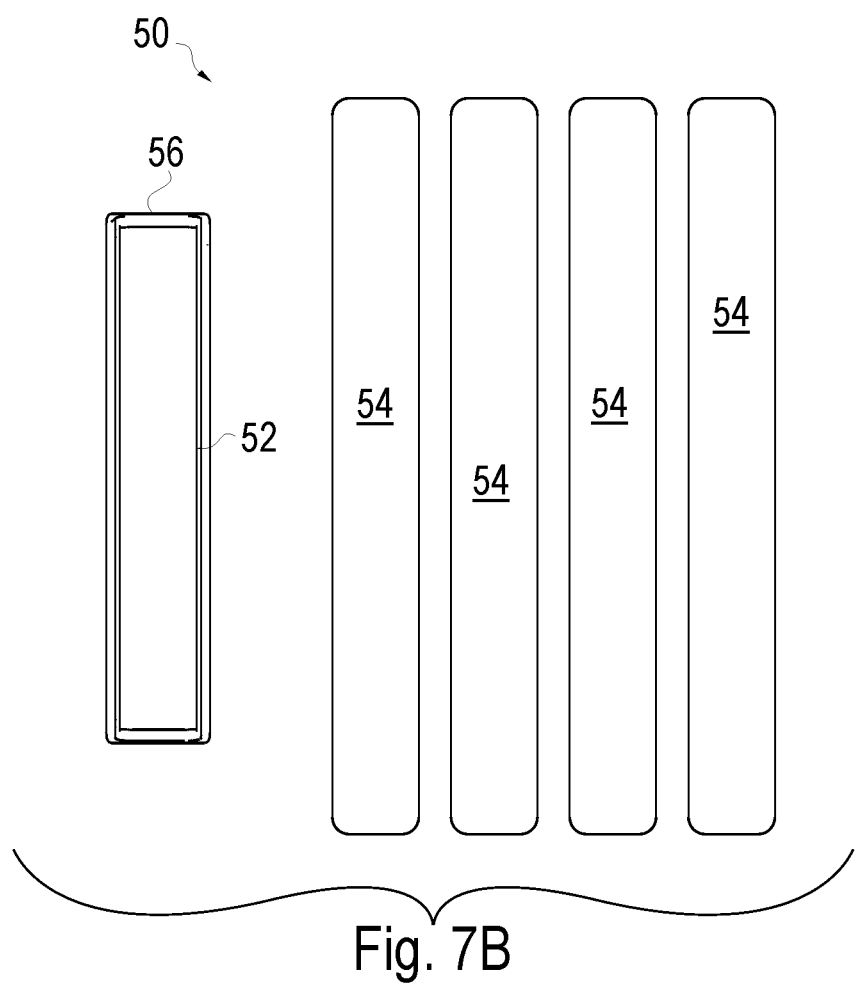
FIG. 7B is a top plan view of the reversible bracelet with inserted panels according to FIG. 7A with the panels removed and four replaceable panels shown adjacent thereto.
Figure 8A:
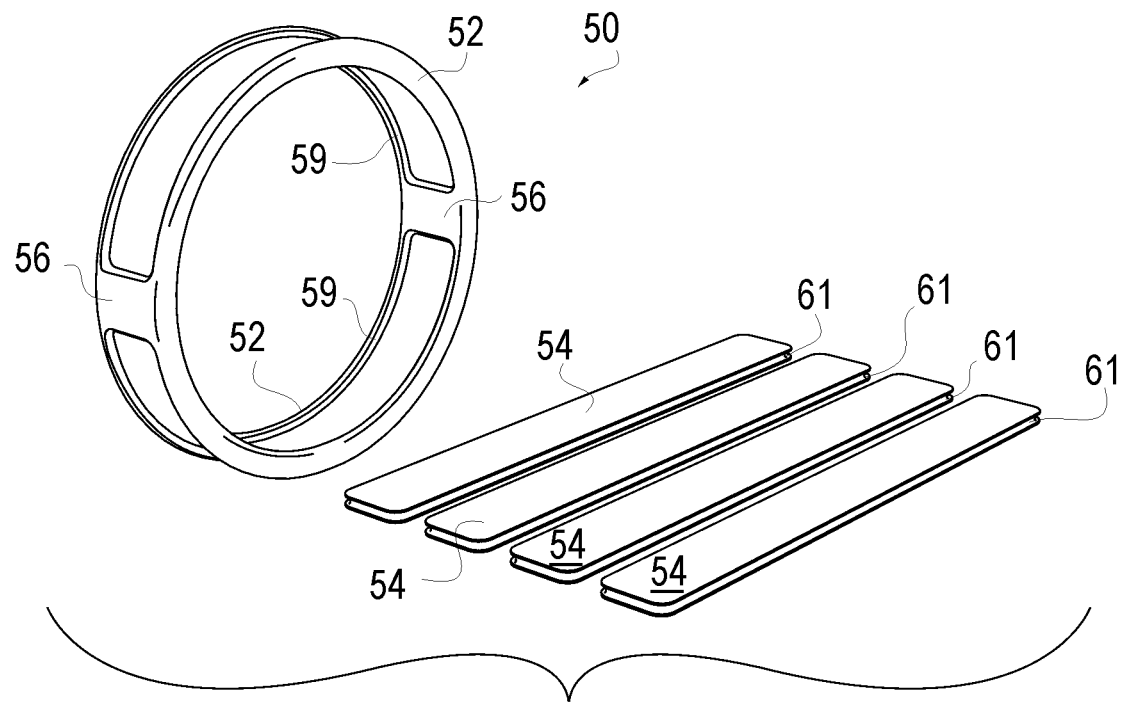
FIG. 8A is a perspective schematic view of a reversible bracelet with inserted panels according to one aspect of the present invention.
Figure 8B:
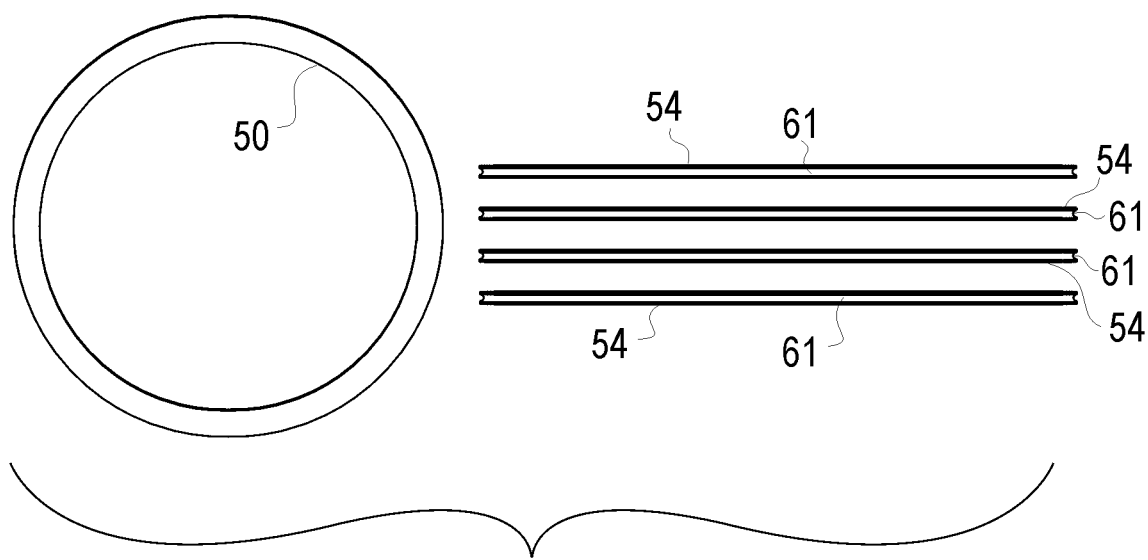
FIGS. 8B and C are side elevation views of the reversible bracelet with inserted panels according to FIG. 8A with the panels removed and four replaceable panels shown adjacent thereto.
Figure 8C:
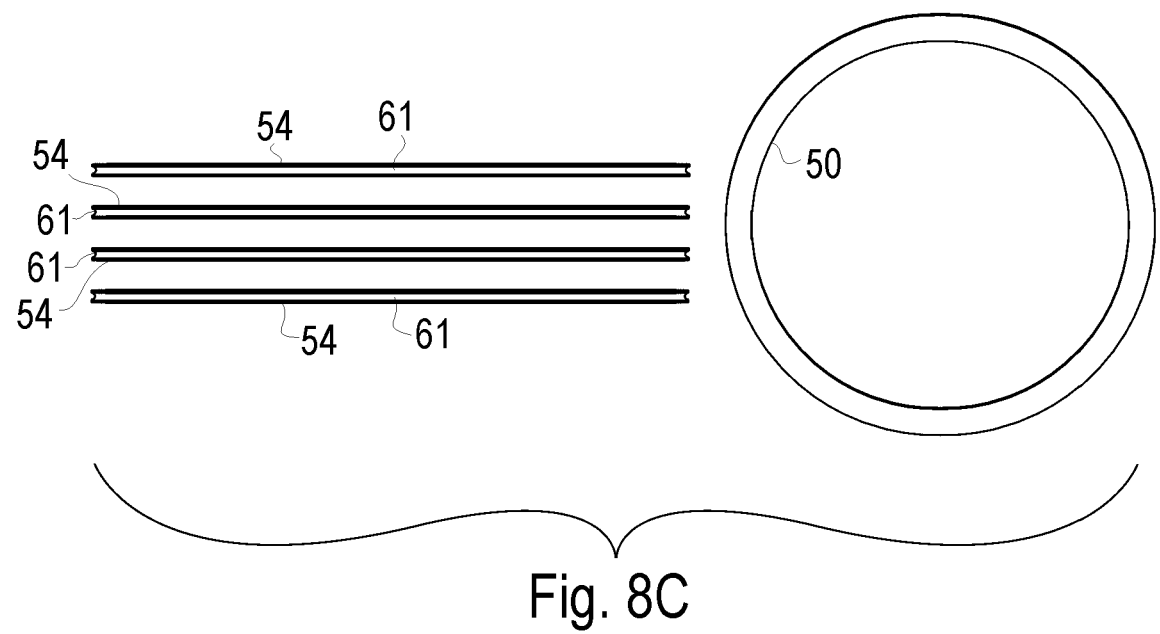
FIG. 8D is a top plan view of a reversible bracelet with inserted panels according to FIG. 8A with the panels removed and four replaceable panels shown adjacent thereto.
FIGS. 8E and F are side elevation views of the reversible bracelet with inserted panels according to FIG. 8A with the panels removed and four replaceable panels shown adjacent thereto.
Figure 8D:
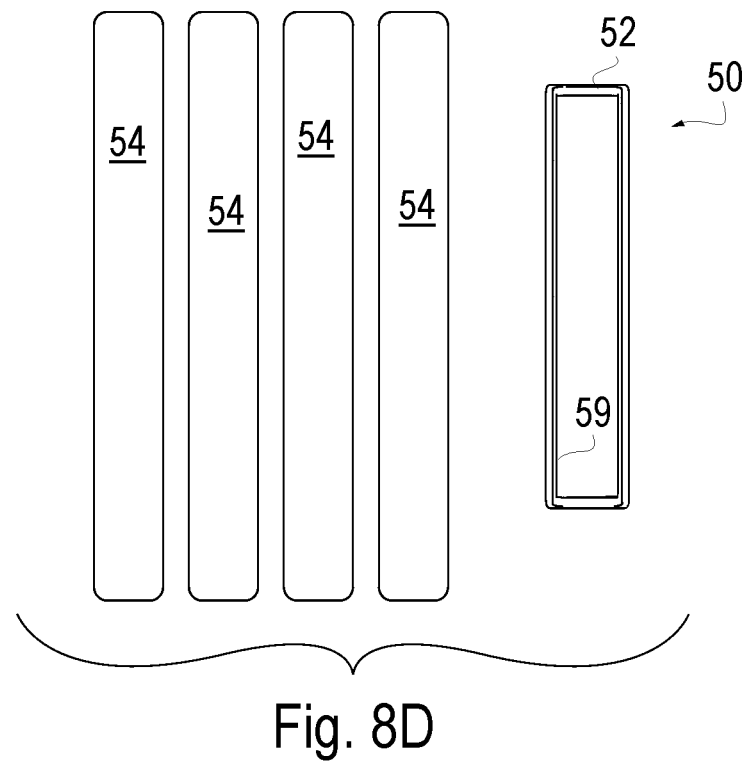
Figure 8E:
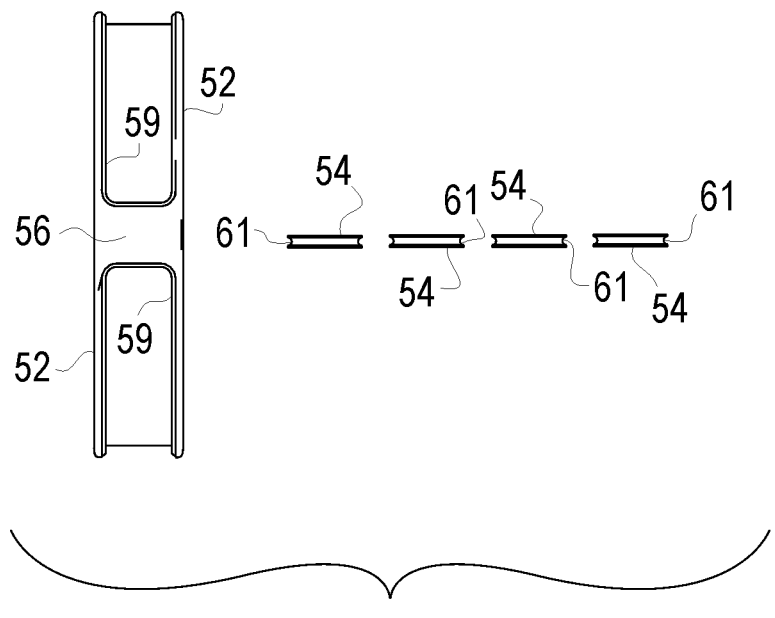
Figure 8F:
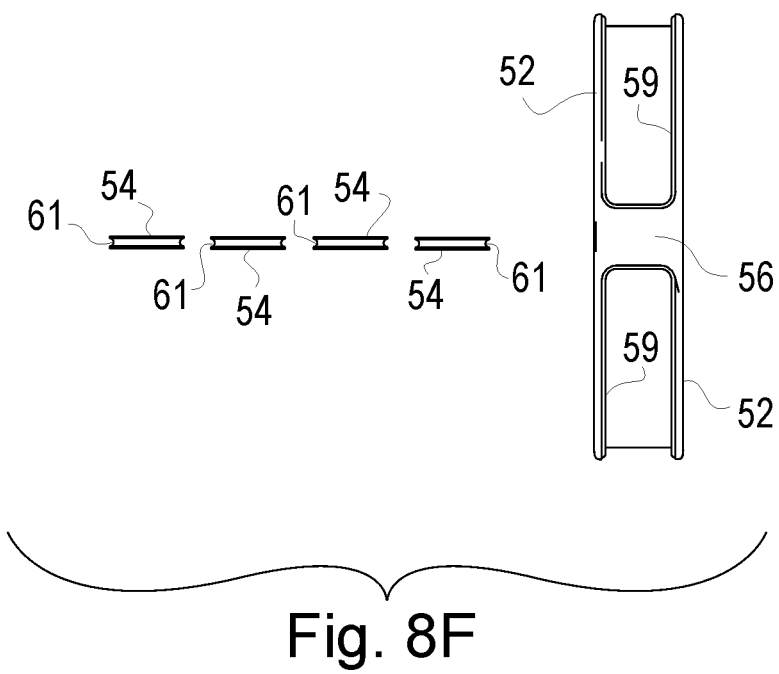

FIG. 7A is a perspective schematic view of a bracelet 50, in this embodiment a reversible bracelet, formed of a series of panel holding frames 52, wherein each frame 52 is designed to hold a panel 54, here a two sided panel 54, therein according to one aspect of the present invention. As discussed below and shown in the figures each frame 52 of the present invention holds an associated panel 52 through a press fit connection, which as known to those in the art may also be described as an "interference fit." Specifically each frame 52 of the present invention holds an associated panel 52 through a snap connection or snap fit, which is defined in the art as a joint or connection in which closure or attachment is achieved over a small lip (element 59). Snap fit connections are common in plastic fields. Further a snap connection or joint is certainly a type of press fit, but not the only type as other interference fits other than snap connections may be press fits. FIG. 7B is a top plan view of the reversible bracelet 50 with inserted panels 54 according to FIG. 7A with the panels 54 removed therefrom and four replaceable panels 54 shown adjacent thereto. FIG. 8A is a perspective schematic view of a reversible bracelet 50 with inserted panels 54 according to another aspect of the present invention. FIGS. 8B and C are side elevation views of the reversible bracelet 50 with inserted panels 54 according to FIG. 8A with the panels 54 removed there-from and four replaceable panels 54 shown adjacent thereto.

The bracelet 50 may be formed of any desired material as known above from the prior panel bracelets 10 and those described in the patent literature. However, it may be advantageous and efficient to form the bracelet 50, and possibly the panels 54, from an elastic material such as silicon or rubber or the like. The use of elastic material allows the bracelet 50 to be formed of a continuous loop in some embodiments, possibly by molding or extruding, with elastic segments or members 56 coupling the frames 52. Alternatively for non-loop constructions, any of a number of clasps 70 may be utilized as known in the art.

Regarding the number of open frames 52, as with frames 12 of the prior art designs, a wide number of frames 52 may be implemented into the bracelet 50. The number of frames 52 is dictated by the length of the bracelet 50 and the size of the individual panels 54. Two panel holding frames 52 and associated panels 54 are shown in the embodiments of FIGS. 7A-B and FIGS. 8A-F merely for illustration, but two identical frames 52 each accommodating substantially rectangular panels 52 is preferred. The "substantially rectangular" panels 54 reference the shape in top or plan view and within the meaning of this application includes panels 54 with parallel ends perpendicular to the width of the bracelet 50 and longer parallel sides extending along the circumference of the bracelet 50. The corners coupling the sides and ends of the panels 54 may have a small radius curve as shown, but still show a substantially rectangular panel 54. Although the bracelet 50 may take a number of particular shapes, a band having a substantially constant width about the circumference is preferred. The constant width bracelet 50 as shown in 7A and other figures together with "substantially rectangular" panels 54 (and associated frames 52) has proven helpful or useful in the display and perception of "informational" panels 54. Informational panels 54 are defined herein as those panels 54 containing text (e.g., player names, team names) and/or logos (e.g. sports team logos). The shape of the bracelet 50, frame 52 and panel 54 provides for a visual orientation of the contained information acting to highlight and improve perception of the informational panel 54.

The general peripheral shape of the panel holding frames 52 is dictated by the shape of the individual panels 54 (which may also be called charms). The peripheral advantageous shape shown is rectangular, but other shapes such as ovals, circular, square, ellipses, triangles, pentagons, hexagons and combinations thereof may be used, but the shape shown is preferred as discussed above. It is the desired peripheral shape of the panels 54 or charms that dictate the shape of the associated frames 52. Further, a single bracelet may, in theory, have distinct shaped frames 52 and panels 54 therein. The use of long rectangle panels 54 and frames 52, as shown, does require a level of flexibility in both the frame 52 and the panels 54 to accommodate the reversibility of the bracelet, if this is to be flipped. Smaller panel sizes would allow more rigid panels 54 to be utilized, but a two panel bracelet 50 is preferred.

As noted the bracelet 50, in the embodiment of FIG. 7A is formed of a series of open insert or panel holding frames 52, wherein each frame 52 is designed to hold a two sided panel 54 therein with each side of the panel 54 including an ornamental design. The specifics of the ornamental design are limitless and can include any design as suggested above in connection with numerous panels 14.

Figure 9:
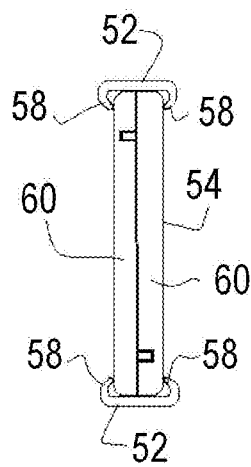
FIG. 9 is a sectional schematic elevation view of a panel holding frame and panel of the bracelet according to FIG. 7A.

As noted above, each open frame 52 may be formed of a rubber or silicon or similar materials including silicon rubber. FIGS. 7A and 7B and 9 have the frame 52 shaped as generally "C" shaped in cross section having arms or extensions 58 as shown in sectional view of FIG. 9 so as to receive and retain one of the two sided panels 54 therein, which may thus be snap or press fit into the frame 52. Where a more rigid material forms the frame 52, then a flexible panel 54 may be used in a similar manner. The flexible materials disclosed can also have a relatively high co-efficient of friction to more securely hold the panels 54.

FIGS. 8A-F have the frame 52 shaped with a retaining bead 59 that is received within a matching groove 61 in the associated panels 54 as shown. In this embodiment the frames 52 with bead 59 also receive and retain one of the two sided panels 54 therein, which may thus be snap or press fit into the frame 52 with the bead 59 engaging the groove 61 of the panel 54. Alternative snap fit couplings may also be implemented.

Alternatively, if rigid materials are desired to be used for both the open frame 52 and the panel 54 then the frame 52 can include a removable side that can allow the panel to slide into place and then have the removed side reattached and secured. Such alternative construction is believed to be within the general knowledge of the jewelry art. However some flexibility in the frames 52 and the panels 54, such as found by using silicon rubber is advantageous.

The flexible construction of the bracelet 50 described allows reversibility, if desired, to be accomplished by having the bracelet 50 flipped in its entirety (i.e. turned inside out). This can also be described as "rolling" the bracelet 50 along the central cylindrical axis, imagine the bracelet 50 on a user's arm and the bracelet is flipped or rolled such that the inner facing surface is now facing outward and vice versa. As an alternative to the closed loop design as shown, each frame 52 may be coupled to adjacent frames 52 via a swivel (not shown) so as to be pivoted relative to the adjacent frame 52 to provide selective reversibility to each respective panel of the bracelet 50.

Figure 10:
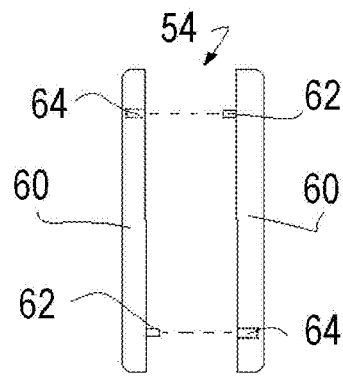
FIG. 10 is a schematic side elevation view of a panel of the bracelet according to FIG. 7A.

FIG. 10 illustrates a construction in which a panel 54 is formed of two separate facing halves 60 that may be coupled together. Press fit, such as snap fit, projection 62 and receiving hole 64 could form the coupling mechanism. The use of one projection 62 and one hole 64 on each half 60 allows the halves to be formed universally allowing the user to couple any two desired halves 60 (rather than forming left and right or male and female parts that limits the combinations). The snap fit design of halves 60 may be easily molded by injection molding with decorative designs added later (via silkscreen printing, or decal or the like). As an alternative magnets on the back of each half 60 could be used for coupling two halves 60 to form a single panel 54.

It is contemplated that the users may wish to leave selective frames empty to give a more open bracelet design. Further it is contemplated that the panels 54 (or panel halves 60) may be designed by the user's themselves in an on-line panel creation system. The panels 54 (or panel halves 60) may have sports motifs or really essentially any theme one can imagine. Informational panels 54 are defined herein as those containing text (e.g., player names, team names) and/or logos (e.g. sports team logos), and as noted above the two substantially rectangular panel 54 design with a constant width bracelet 50 is advantageous for informational panels 54. The panels 54 (or panel halves 60) may be formed as watches, key-holding units, electronic devices (e.g., pulse measuring/recording/transmitting device, temperature measuring/recording/transmitting device), sports or other trading cards, panels that are convertible to toys, Photos (family photos), Mirror, Glow in the dark inserts, etc.

The snap fit panel holding frames 52 can be expanded beyond bracelet construction as shown. The same construction of frame and inserted double faced panel 52 may be easily utilized as a necklace, or as a broach or earring. Outside of the jewelry art, the frame 52 may be used as, in larger form, a simple picture frame as well.

Figure 11A:
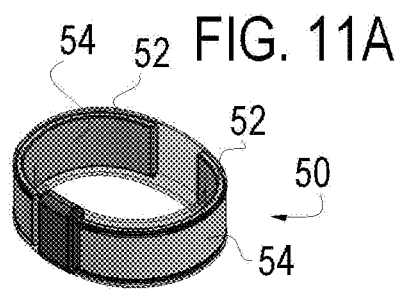
FIG. 11A is a perspective schematic view of a bracelet with inserted panels according to one aspect of the present invention.
Figure 12A:
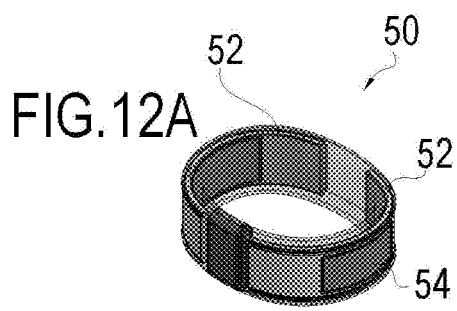
FIG. 12A is a perspective schematic view of a bracelet with inserted panels according to one aspect of the present invention.
Figure 11B:
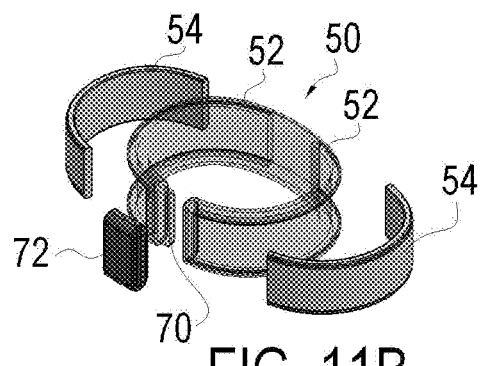
FIG. 11B is an exploded perspective schematic view of a bracelet with inserted panels of FIG. 11A.
Figure 12B:
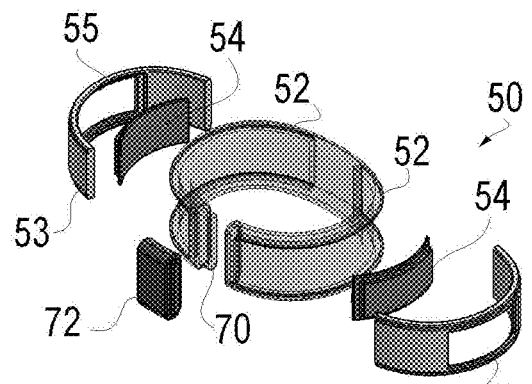
FIG. 12B is an exploded perspective schematic view of a bracelet with inserted panels of FIG. 12A.
Figure 13:
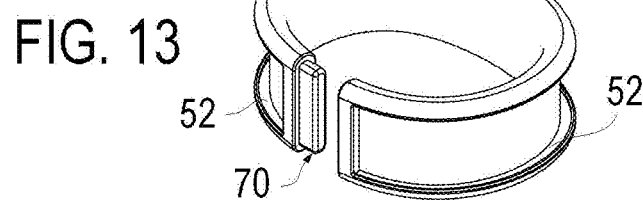
FIG. 13 is a perspective schematic view of a bracelet body having two panel holding frames for forming the bracelet with inserted panels of FIGS. 11A and 12A.

FIG. 11A is a perspective schematic view of a bracelet 50 with inserted panels 54 according to one aspect of the present invention and FIG. 11B is an exploded perspective schematic view thereof. Similarly FIG. 12A is a perspective schematic view of a bracelet 50 with inserted panels 54 according to one aspect of the present invention and FIG. 12B is an exploded perspective schematic view of this bracelet 50. FIG. 13 is a perspective schematic view of a common bracelet body having two panel holding frames 52 for forming the bracelet 50 with inserted panels 54 of FIGS. 11A and 12A.

The bracelet of FIGS. 11A and 12A are similar to those described above in connection with FIGS. 7 and 8. Here the body of the bracelet 50, and some of the panels 54, are formed from an elastic material such as silicon or rubber or the like. The body of the bracelet as shown is formed clear or semi-transparent such that the panel holding frames 52 may have a backing on one side, whereby the reverse side of the two sided panel 54 will be seen through the clear or semi-transparent back.

The general peripheral shape of the panel holding frames 52 for the embodiments of FIGS. 11A-B and FIGS. 12A-B is preferably rectangular, as shown. The snap-fit panel and frame construction discussed above is preferred. The frames 52 of FIGS. 11A-B and 12A-B have the frame shaped as generally "C" shaped in cross section having arms or extensions (as shown in sectional view of FIG. 9 so as to receive and retain one of the two sided panels 54 therein), which may thus be snap or press fit into the frame 52. As noted above the flexible materials disclosed can also have a relatively high co-efficient of friction to more securely hold the panels 54.

Figure 16:
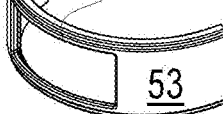
FIG. 16 is a perspective schematic view of an adaptor or extender for selective use with the bracelet with inserted panels of FIGS. 11A and 12A.

The bracelet 50 of FIGS. 11A-B and 12A-B further includes the use of a snap fit male-female clasp 70 for easily opening and closing the bracelet 50 for placing on the user. An adaptor or extender 72, shown individually in FIG. 16, allows the bracelet 50 to accommodate a variety of sizes, and the use of more than one extender 72, or extenders of various lengths are also contemplated.

Figure 14:
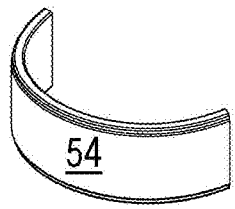
FIG. 14 is a perspective schematic view of a panel for use with the bracelet with inserted panels of FIG. 11A.
Figure 15B:
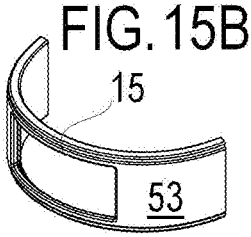
FIG. 15B is a perspective schematic view of a panel cover for use with the bracelet with inserted panels of FIG. 12A.
Figure 15A:
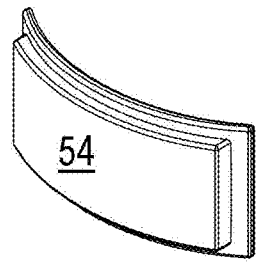
FIG. 15A is a perspective schematic view of a panel for use with the bracelet with inserted panels of FIG. 12A.

The bracelets 50 of FIGS. 11A-B and 12A-B both use a common body shown in FIG. 13 but differ in the sized panels 54 that are used. The bracelets 50 of FIGS. 11A-B uses arcuate panels substantially rectangular 54 filling the frame 52 and these are shown in FIG. 14. The bracelets 50 of FIGS. 11A-B uses arcuate panels 54 that may be shorter than the frame 52 and these are shown in FIG. 15A. The bracelets 50 of FIGS. 11A-B further uses a panel cover 53 having an insert window 55 for use with the bracelet with inserted panels of FIG. 12A. The panel cover 53 will snap onto the body of bracelet 50 similar to the panel 54 and can be used to further lock the panel 54 in place. Further the panel 54 may extend into the window 55 of the cover 53. The cover 53 and the body of the bracelet 50 forming the frame 52 combine to sandwich the panel 54 there-between and allow for greater securing of the panel 54. Further distinct covers 53 can be adapted for distinct panels 54 to increase the size and types of panels 54 that may be associated with a given bracelet 50.

Figure 17B:
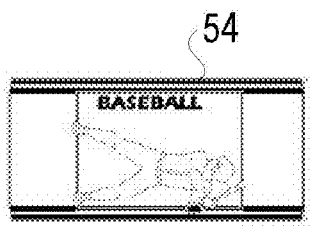
FIGS. 17A-H are perspective schematic views of alternative utilitarian panels for the bracelet use with the bracelet with inserted panels of FIGS. 11A and 12A.
Figure 17C:
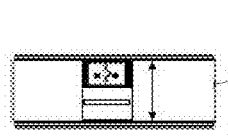
Figure 17A:
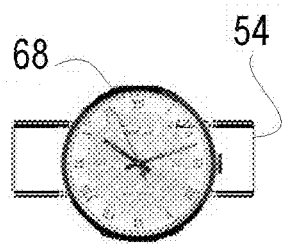

FIGS. 17A-H demonstrate that the panels 54 may include a variety of utilitarian aspects aside from mere decoration. For example the panels 54 may include electronic components such as watches, as shown in FIG. 17A, and such a panel 54 may have a portion 68 of the panel 54 extends beyond the frame 52 to give more versatility to the desired panels 52. Care must be taken when designing portions 68 that extend beyond the frame 52 that the portion 68 does not interfere substantially with either to connection between the panel 54 and frame 52 or the reversibility of the bracelet 50, if reversibility is desired.

As discussed above the panels may be in the form of a collectable element, namely a sports card or gaming card as shown in FIG. 17B, which as referenced above is a type of informational panel 54.

Figure 20A:
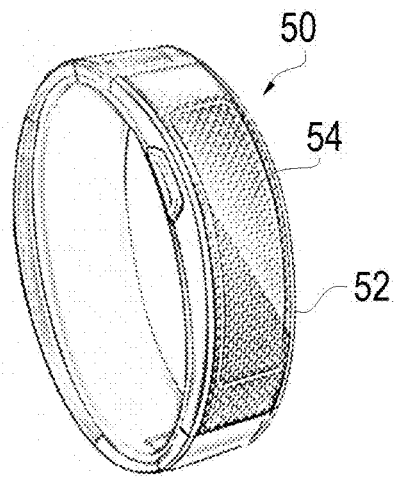
FIGS. 20A and B are perspective views of a bracelet with an alternative USB port panel according to FIG. 18A.
Figure 20B:
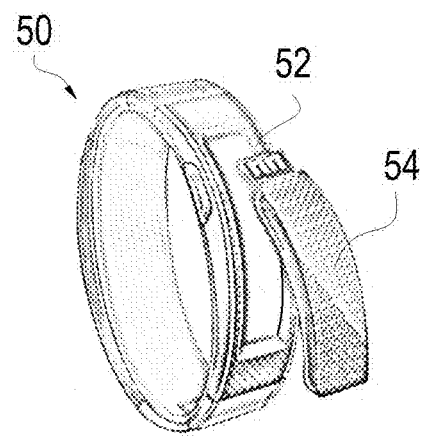

FIG. 17C schematically illustrates the inclusion of a USB key (also called a memory stick) incorporated into a panel 54. A different version of this type of panel 54 is shown in FIGS. 20A and B. In use the panel can be popped out of the frame 12 and the USB engaging member slid laterally out of the side edge of the panel 54 and the memory stick installed in a USB port of a computer. The function and structure of a USB member, and the slide mechanism therefore, is known in the art. In this configuration a whole in the side of the bracelet body allowing the USB member to slide through would allow the panel 54 to be used without removing it from the frame 52. Alternatively a flip up engagement member may be utilized.

Figure 17H:
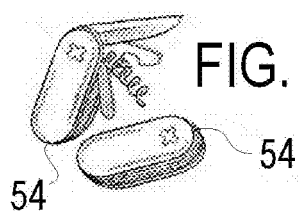
Figure 17E:
Figure 17F:
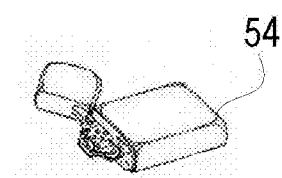
Figure 17G:
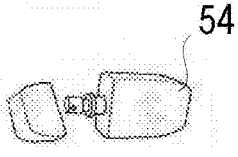
Figure 17D:

FIG. 17D schematically illustrates the inclusion of electronic sensors and user display incorporated into a panel 54, which track user bio-signals (pulse rate, breath rate, ekg and the like), such as found in FITBIT® brand sensors or trackers. This can be useful for monitoring a user's activity during the day or during specific exercise periods and these may communicate with other devices, such as with a user's health related application on a smart phone (e.g. a MAP-MYRUN® exercise tracking application) or with an exercise machine (treadmill). Further details of the use and application of this type of sensors in this panel 54 are found in reviewing the FITBIT® brand trackers.

FIG. 17E schematically illustrates the inclusion of a barcode or other optical scanned code incorporated into a panel 54 and is another type of informational panel 54. The barcode in this panel 54 will typically be a user identification bar code such as a hospital user ID band, employee ID, school ID, or a gym membership identification or the like. Both the gym membership and the hospital ID band ID panels 54 applications for this panel 54 may be particularly well suited to be paired with the biometric sensor panels of FIG. 17D.

In the hospital application the patient may be given a bracelet 50 with a personal ID panel 54 as shown in FIG. 17E, which panel 54 is made up for the specific patient (e.g. a label with barcode ID is created and attached to a blank panel 54), and the other panel 54 of bracelet 50 includes desired biometric sensors such as discussed in connection with FIG. 17D wherein the patient's heart rate, ekg, breath rate or the like may be measured with an appropriate sensor including panel 54 discussed in association with FIG. 17D and tied to the patient associated with the ID panel 54 of FIG. 17E.

In a gym membership example the member may be given a bracelet 50 with a personal membership ID panel 54 as shown in FIG. 17E, which panel 54 is made up for the specific member (e.g. a label with barcode ID is created and attached to a blank panel 54), and the other panel 54 of bracelet 50 includes desired exercise biometric sensors discussed in connection with FIG. 17D. When entering the gym the user can scan the ID to gain access and to have the specific exercises and results of the member measured and associated with that member (via particular machines or exercise classes or the like). The gym, the member and/or personal trainers can utilize the information to more precisely direct the member's workouts to maximize the effects. The bracelet 50 becomes more than a gym access device and a tool to facilitate the goals of the individual and the gym. Different sensing via distinct panels 54 or different analysis of the data may be made available at different costs and or different membership levels to give the gym some greater monetization opportunities.

FIG. 17F schematically illustrates the inclusion of a lighter incorporated into a panel 54, while FIG. 17H schematically illustrates the inclusion of a series of tools into a panel 54 (e.g. in the manner of a Swiss army knife). These panels 54 may be combined to form a desired utilitarian bracelet, i.e. a camper's bracelet.

FIG. 17G schematically illustrates the inclusion of a pump spray container incorporated into a panel 54. This panel 54 may be sufficient to hold a desired amount of women's perfume or men's cologne. Any fluid that a user may desire to have a periodic but immediate use of could be used, such as breath spray (for dating), bug spray (for camping), sun screen (for any outdoor activity), and medicaments (e.g. Albuterol, a bronchodilator, for patients).

Other utilities for panels 54 include the functions of a cell phone, such as camera, flashlight, recorder, transmitter, and other phone functions. Other configurations include safety lights (for pedestrians and/or bicyclists) in panels 54; or Pens, Pencils, Highlighter in a panel 54 (e.g. for golfers); glow in the dark elements in a panel 54 (great for nighttime concerts or amusement parks patrons); and a number of other items such as the tool shown in FIG. 17H. The bracelet 50 gives a useful platform for a multitude of applications with designated panels 54.

FIGS. 18A-I illustrate a bracelet with inserted panels according to one preferred embodiment of the present invention. The bracelet 50 is formed of a pair of panel holding frames 52, wherein each frame 52 is designed to hold a panel 54 through a press fit connection, specifically a snap connection or snap fit. The frame 52 includes a top retaining bead 59 that is received within a matching top edge peripheral groove 61 in the associated panels 54 as shown. It is deemed advantageous and efficient to form the bracelet 50 of this embodiment, and possibly the panels 54, from an elastic material such as silicon rubber or the like.

The bracelet 50 of FIGS. 18A-I includes a male-female magnetic clasp 70, the construction of which is generally known in the art as shown in U.S. Pat. No. 8,884,100, which is incorporated herein by reference. The prior art clasps have implemented magnetic members associated with both the male and female components, but this unnecessarily increases the cost of the clasp. A single magnet is sufficient for forming the clasp with a corresponding element formed of magnetic material (e.g. steel).

Figure 1:
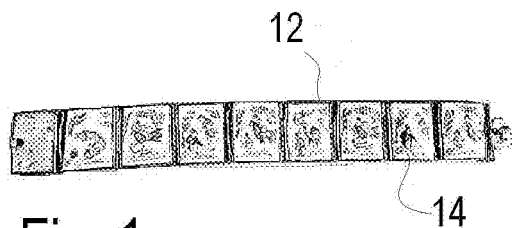
FIGS. 1-6 illustrate prior art panel bracelet designs.
Figure 2:
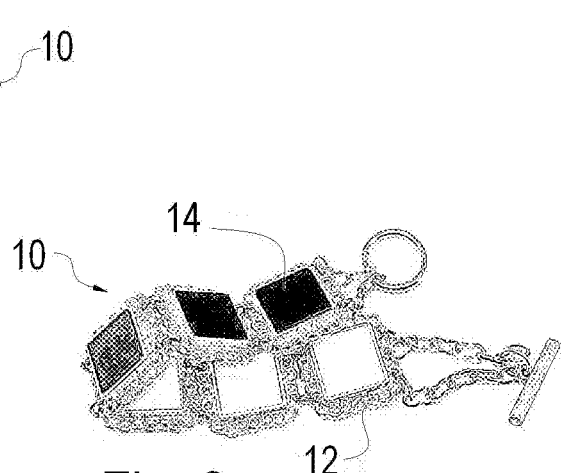
Figure 3:
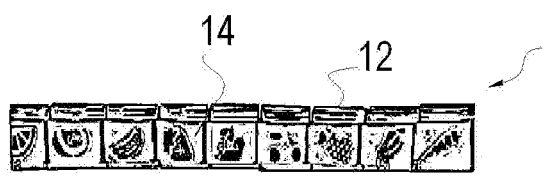
Figure 4:
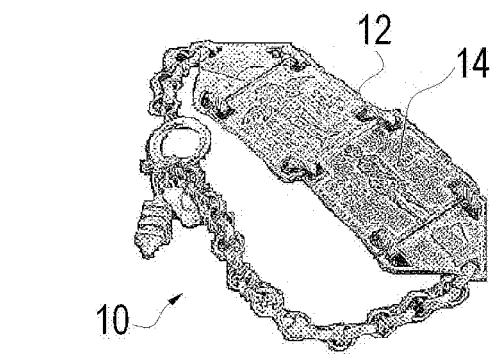
Figure 5:
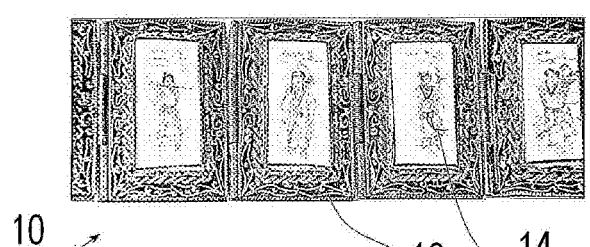
Figure 6:
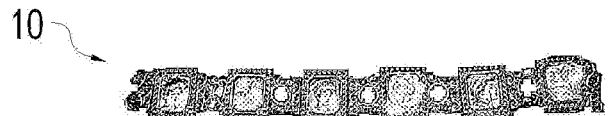

The bracelet 50 of FIGS. 18A-I incorporates two substantially rectangular panel holding frames 52 each extending of over 130 degrees along the circumference of the bracelet 50 (about 133 degrees) and associated substantially rectangular panels 54 whereby the panels 54 include parallel ends perpendicular to the width of the bracelet 50 and longer parallel sides extending along the circumference of the bracelet 50 (extending over 130 degrees). The corners coupling the sides and ends of the panels 54 have a small radius curve as shown, but still show a substantially rectangular panel 54. The bracelet 50 of FIGS. 18A-1 has a substantially constant width about the circumference, which together with the substantially rectangular panels 54 (and associated frames 52) has proven useful in the display and perception of "informational" panels 54 by providing for a visual orientation or cue for the contained information acting to highlight and improve perception of the informational panel 54.

Figure 19A:
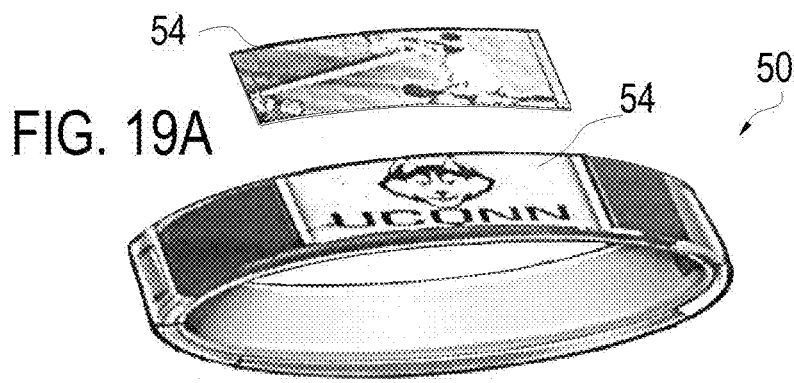
FIGS. 19A and B are perspective views of a sports motif bracelets and interchangeable panels according to FIG. 18A.
Figure 19B:
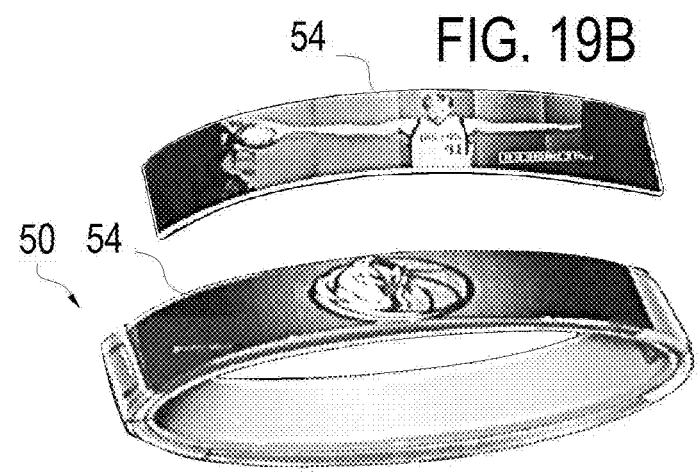

FIGS. 19A and B are perspective views of a sports motif bracelets 50 with interchangeable panels 54 according to bracelet construction of FIGS. 18A-I. FIGS. 20A and B are perspective views of a bracelet with an alternative USB port panel (similar to FIG. 17C) with the bracelet 50 shown in FIGS. 18A-I.

The scope of the invention is not to be limited by the illustrative examples described above. The scope of the present invention is defined by the appended claims and equivalents thereto.

What is claimed is:

1. A reversible panel bracelet comprising:
a reversible body;
a plurality of two sided panels configured to be selectively replaceable within the body of the bracelet and with each side of the panel including an ornamental design;
at least two open panel holding frames forming at least part of the reversible body of the bracelet, wherein each open panel holding frame includes a central opening through the reversible body of the bracelet and is designed to hold a two sided panel therein; and
wherein each panel holding frame is one of i) generally "C" shaped in cross section to receive and retain one of the two sided panels therein and which are placed within the open panel holding frame by engaging with two opposing faces of the panel, or ii) includes a retaining bead that is received within a matching groove in a perimeter of a panel held within the open panel holding frame to receive and retain one of the two sided panels therein.

2. The reversible panel bracelet with inserted two sided panels according to claim 1 wherein exactly two substantially rectangular panel holding frames are provided in the reversible body of the panel bracelet.

3. The reversible panel bracelet with inserted two sided panels according to claim 1 wherein the open panel holding frames are formed of elastic material and wherein the reversible body of the bracelet is configured to be flipped in its entirety.

4. The reversible panel bracelet with inserted two sided panels according to claim 1 wherein at least one of the panels is formed of two separate facing halves coupled together.

5. The reversible panel bracelet with inserted two sided panels according to claim 1 wherein the panels include at least one of a functioning watch, a key-holding unit, an electronic device, and a sports trading card.

6. A panel bracelet comprising:
a body having a width and a circumference;
a plurality of panels configured to be selectively replaceable within the body of the bracelet, wherein each panel includes parallel ends configured to be perpendicular to the width of the body of the bracelet and longer parallel sides configured to extend along the circumference of the body of the bracelet, wherein each panel includes a perimeter groove around the perimeter of the panel;
a pair of panel holding frames forming at least part of the body of the bracelet, wherein each open panel holding frame is configured to hold a panel therein, and wherein each panel holding frame includes a retaining bead that is received within the perimeter groove of a panel held within the panel holding frame to receive and retain the panel therein, and wherein each panel holding frame extends of over 130 degrees along the circumference of the body of the bracelet.

7. A panel bracelet comprising:
a body having a width and a circumference;
a plurality of panels configured to be selectively replaceable within the body of the bracelet, wherein each panel includes parallel ends configured to be perpendicular to the width of the body of the bracelet and longer parallel sides configured to extend along the circumference of the body of the bracelet, wherein each panel includes a perimeter groove around the perimeter of the panel;

a pair of panel holding frames forming at least part of the body of the bracelet, wherein each open panel holding frame is configured to hold a panel therein, and wherein each panel holding frame includes a retaining bead that is received within the perimeter groove of a panel held within the panel holding frame to receive and retain the panel therein, and wherein at least one panel is a collectable sports related element including informational text thereon.

8. A panel bracelet comprising:

a body having a width and a circumference;

a plurality of panels configured to be selectively replaceable within the body of the bracelet, wherein each panel includes parallel ends configured to be perpendicular to the width of the body of the bracelet and longer parallel sides configured to extend along the circumference of the body of the bracelet, wherein each panel includes a perimeter groove around the perimeter of the panel;

a pair of panel holding frames forming at least part of the body of the bracelet, wherein each open panel holding frame is configured to hold a panel therein, and wherein each panel holding frame includes a retaining bead that is received within the perimeter groove of a panel held within the panel holding frame to receive and retain the panel therein, and wherein at least one panel includes a USB key.

9. A panel bracelet comprising:

a body having a width and a circumference;

a plurality of panels configured to be selectively replaceable within the body of the bracelet, wherein each panel includes parallel ends configured to be perpendicular to the width of the body of the bracelet and longer parallel sides configured to extend along the circumference of the body of the bracelet, wherein each panel includes a perimeter groove around the perimeter of the panel;

a pair of panel holding frames forming at least part of the body of the bracelet, wherein each open panel holding frame is configured to hold a panel therein, and wherein each panel holding frame includes a retaining bead that is received within the perimeter groove of a panel held within the panel holding frame to receive and retain the panel therein, and wherein at least one panel includes a user identifying barcode.

10. A panel bracelet comprising:

an elastomeric body having exactly two substantially rectangular panel holding frames, wherein each frame is designed to hold a panel therein, and wherein each panel holding frame is one of i) generally "C" shaped in cross section to receive and retain one of the panels therein by engaging with two opposing faces of the panel, or ii) includes a retaining bead that is received within a matching groove in the perimeter of an associated panel to receive and retain one of the panels therein, and a plurality of panels removeably secured within the rectangular panel holding frames, wherein the plurality of panels include at least two from the group i) a panel which includes electronic components, ii) a panel which includes a watch, iii) a panel which is in the form of a collectable sports related element, iv) a panel which includes a USB key, v) a panel which includes at least one biometric sensor, vi) a panel which includes a user identifying barcode, vii) a panel which includes a lighter, viii) a panel which includes a series of tools folded into the panel, and ix) a panel which includes a pump spray container, and wherein at least one panel is formed of two halves coupled together.

* * * * *